(12) United States Patent
Mertens et al.

(10) Patent No.: US 8,470,293 B2
(45) Date of Patent: Jun. 25, 2013

(54) METHOD OF PREPARING A MOLECULAR SIEVE AND ITS USE IN THE CONVERSION OF OXYGENATES TO OLEFINS

(75) Inventors: Machteld M. Mertens, Boortmeerbeek (BE); Chunshe Cao, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 353 days.

(21) Appl. No.: 12/916,964

(22) Filed: Nov. 1, 2010

(65) Prior Publication Data
US 2011/0152478 A1 Jun. 23, 2011

Related U.S. Application Data

(60) Provisional application No. 61/287,839, filed on Dec. 18, 2009.

(51) Int. Cl.
*C01B 39/54* (2006.01)
*B01J 29/85* (2006.01)
*C07C 1/24* (2006.01)

(52) U.S. Cl.
CPC .......... *C01B 39/54* (2013.01); *B01J 29/85* (2013.01); *C07C 1/24* (2013.01); *Y10S 423/30* (2013.01)
USPC .......... 423/702; 423/704; 423/705; 423/706; 423/708; 423/DIG. 30; 423/305; 502/60; 502/214; 585/640

(58) Field of Classification Search
USPC .......... 423/702, 704, 705, 706, 707, 709, 423/305, DIG. 30; 502/60, 214; 585/640
See application file for complete search history.

(56) References Cited

U.S. PATENT DOCUMENTS

| | | | |
|---|---|---|---|
| 4,440,871 A | 4/1984 | Lok et al. | |
| 5,952,538 A * | 9/1999 | Vaughn et al. | 585/640 |
| 6,121,503 A * | 9/2000 | Janssen et al. | 585/640 |
| 6,620,983 B1 | 9/2003 | Cao et al. | |
| 6,974,889 B1 | 12/2005 | Verduijn et al. | |
| 6,984,765 B2 | 1/2006 | Reyes et al. | |
| 7,094,389 B2 | 8/2006 | Cao et al. | |
| 2004/0215044 A1 | 10/2004 | Mertens et al. | |
| 2006/0292053 A1 | 12/2006 | Mertens et al. | |
| 2008/0045767 A1 | 2/2008 | Cao et al. | |

FOREIGN PATENT DOCUMENTS

| WO | 00/06493 | 2/2000 |
|---|---|---|
| WO | 2007/130231 | 11/2007 |
| WO | 2010/011420 | 1/2010 |

OTHER PUBLICATIONS

Hereijgers B P C et al., "Product shape selectivity dominates the Methanol-to-Olefins (MTO) reaction over H-SAPO-34 catalysts", Journal of Catalysis, Academic Press, Duluth, MN, US, vol. 264, No. 1, pp. 77-87.

* cited by examiner

*Primary Examiner* — David M Brunsman
(74) *Attorney, Agent, or Firm* — Kevin M. Faulkner; Ronald Pols

(57) ABSTRACT

A method of preparing a silicoaluminophosphate molecular sieve which comprises the steps of combining a source of silica, a source of phosphorous, a source of alumina and water to form a primary mixture; adding a structure directing agent to said mixture and optional seeds to form a synthesis mixture. The synthesis mixture is synthesized by heating the mixture to a crystallization temperature to form the sieve. The molar ratio of the structure directing agent relative to the source of alumina may vary between 1.3 and 1.9 and the ratio of water to the source of alumina may vary between 20 to 34.

17 Claims, 1 Drawing Sheet

METHOD OF PREPARING A MOLECULAR SIEVE AND ITS USE IN THE CONVERSION OF OXYGENATES TO OLEFINS

CROSS-REFERENCE TO RELATED APPLICATION

The present application claims priority to Provisional Patent Application No. 61/287,839 filed Dec. 18, 2009, which is incorporated herein by reference.

FIELD OF THE INVENTION

This invention relates to a method of preparing a silicoaluminophosphate molecular sieve, and a method of converting hydrocarbons, and oxygenates in particular, into olefins, particularly ethylene and/or propylene, using said molecular sieve.

BACKGROUND OF THE INVENTION

Over the last two decades, many catalytic materials have been identified as being useful for carrying out oxygenates-to-olefins ("OTO") reactions. Nowadays, crystalline molecular sieves are the preferred catalysts because of their performance in OTO conversion and ease of large scale manufacture. Particularly preferred materials are eight-membered ring aluminosilicates, such as those having the chabazite (CHA) framework type, as well as aluminophosphates (AlPOs) and silicoaluminophosphates (SAPOs) of the CHA framework type, such as SAPO-34.

In U.S. Pat. No. 4,440,871, the synthesis of a wide variety of SAPO materials of various framework types is described, using various organic templates or structure directing agents. Also of interest are U.S. 2008-0045767, U.S. Pat. No. 7,094,389 and U.S. Pat. No. 6,984,765.

PCT/US2009/046154 discloses a method of preparing a silicoaluminophosphate molecular sieve by combining a source of phosphorus, a source of alumina, a liquid and a structure directing agent to form a synthesis mixture. This mixture is crystallized to produce a silicoaluminophosphate molecular sieve which has 90% or greater of a CHA framework type character. These sieves can be synthesized on the basis of a number of silica sources such as silica sols and colloidal silica sols.

Despite considerable research efforts in the identification of suitable catalysts for OTO applications, to date the yields for producing these catalysts, their performance and process efficiency including their use of resources has been compromised. This has impacted on the overall economic performance of OTO processes.

The present invention aims to obviate or at least mitigate the above described problems, and/or to provide improvements generally.

SUMMARY OF THE INVENTION

According to the invention there is provided a method of preparing a silicoaluminophosphate molecular sieve, a method of converting hydrocarbons into olefins and a method of forming an olefin based polymer product as defined in any one of the accompanying claims.

In an embodiment of the invention, there is provided a method of preparing a silicoaluminophosphate molecular sieve, comprising:

a) combining a source of silica ($SiO_2$), a source of phosphorous (P), a source of alumina ($Al_2O_3$), and water ($H_2O$) to form a primary mixture;

b) adding a structure directing agent (R) to said primary mixture and optional seeds to form a synthesis mixture; and c) heating said synthesis mixture to a crystallization temperature to form the molecular sieve, wherein the molar ratio of structure directing agent relative to the source of alumina $R/Al_2O_3$ is ranging from 1.3 to 1.9.

We have discovered that for a narrow molar ratio of the structure directing agent in relation to the source of alumina, $R/Al_2O_3$ ranging from 1.3 to 1.9, the silicoaluminophosphate molecular sieve of the invention can be prepared at an improved yield, whereby the prime olefin selectivity ("POS"), which is defined as the sum of the wt % of ethylene and propylene in the reaction product mixture, is also optimized. In particular for a narrow molar ratio of the structure directing agent in relation to the source of alumina, $R/Al_2O_3$ ranging from 1.3 to 1.9 in combination with a ratio of water to alumina $H_2O/Al_2O_3$ ranging from 20 to 34, the yield of silicoaluminophosphate molecular sieve is optimized, whereby the prime olefin selectivity ("POS"), which is defined as the sum of the wt % of ethylene and propylene in the reaction product mixture, is also optimized.

We have further found that for silica to alumina molar ratios $SiO_2/Al_2O_3$ ranging from 0.05 or 0.10 to 0.15 or 0.20 or 0.30 or 0.35, the values for both POS and yield are further optimized.

None of these narrow, optimized ranges either alone, or in combination, together with the associated improvements in both POS and catalyst yield, were evident from the above cited document PCT/US2009/046154. In particular, for a silica source comprising a colloidal silica, these improvements are particularly evident.

An additional beneficial effect associated with the invention as disclosed herein is that a reduced quantity of template or structure directing agent is needed to produce the silicoaluminophosphate molecular sieve according to the invention. It is well known that structure directing agents are relatively expensive materials in comparison to other feed sources for preparing a molecular sieve.

In addition, after synthesis of the molecular sieve, to prepare the catalyst for its application in an OTO conversion process, it is preferable that the template be removed. This is conducted by calcining, whereby the template is effectively decomposed upon removal. Currently, no technology is viable which would enable the removed template to be reused. So the more template is used in the synthesis of the molecular sieve, the more expensive the overall cost for producing the molecular sieve. Furthermore, due to their chemical composition, removed templates can also present an environmental problem as the structure directing agent contains toxic components which are released during template removal from the crystallized molecular sieves.

In another embodiment, there is provided a silicoaluminophosphate molecular sieve crystallized from a synthesis mixture comprising a source of silica ($SiO_2$), a source of phosphorus, a source of alumina ($Al_2O_3$), water ($H_2O$), a structure directing agent (R) and optional seeds, wherein the molar ratio of structure directing agent relative to the source of alumina $R/Al_2O_3$ ranges from 1.3 to 1.9 and the ratio of water to the source of alumina $H_2O/Al_2O_3$ ranges from 18 to 34, said sieve comprising a crystal size distribution such that the average crystal size is between 0.7 and 2.2 µm, preferably between 0.9 and 2.0 µm. The molecular sieve preferably comprises a colloidal silica source.

In yet another embodiment of the invention, there is provided a method of converting hydrocarbons into olefins comprising a) preparing a silicoaluminophosphate molecular sieve as defined herein; b) formulating the silicoaluminophosphate molecular sieve, along with a binder and optionally a matrix material into a silicoaluminophosphate molecular sieve catalyst composition comprising from at least 10% to 50% molecular sieve; and c) contacting said catalyst composition with a hydrocarbon feed under conditions sufficient to convert said hydrocarbon feed into a product comprising predominantly one or more olefins.

Finally, in a further embodiment of the invention, there is provided a method of forming an olefin based polymer product comprising a) preparing a silicoaluminophosphate molecular sieve; b) formulating said silicoaluminophosphate molecular sieve along with a binder and optionally a matrix material, into a silicoaluminophosphate molecular sieve catalyst composition comprising from at least 10 to 50 wt % of a molecular sieve; c) contacting said catalyst composition with a hydrocarbon feed under conditions sufficient to convert said hydrocarbon feed into a product comprising predominantly one or more olefins; and d) polymerizing at least one or more olefins optionally with one or more comonomers and optionally in the presence of a polymerization catalyst, under conditions sufficient to form an olefin based copolymer.

DETAILED DESCRIPTION OF THE EMBODIMENTS

Figure 1:
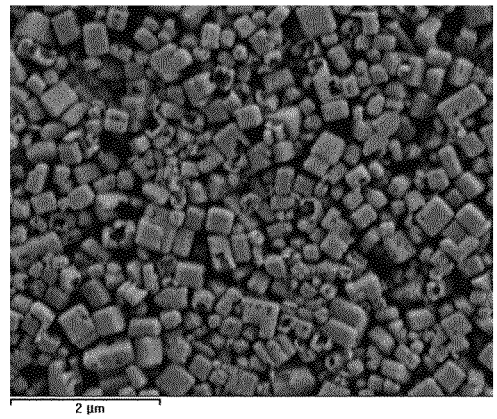
FIG. 1 shows a scanning electron micrograph (SEM) corresponding to Sample B4 of Example B.

According to an embodiment of the present invention there is provided a method of preparing a silicoaluminophosphate molecular sieve which comprises the steps of combining a source of silica, a source of phosphorous, a source of alumina and water to form a primary mixture; adding a structure directing agent to said mixture and optional seeds to form a synthesis mixture. The synthesis mixture is synthesized by heating the mixture to a crystallization temperature to form the sieve. The molar ratio of the structure directing agent relative to the source of alumina may vary between 1.3 and 1.9 and the ratio of water to the source of alumina may vary between 20 to 34.

We have discovered that for narrow ranges for both the structure directing agent relative to the source of alumina and the ratio of water to the source of alumina, the prime olefin selectivity, and yield of the molecular sieve is improved. In this context, we stress that even seemingly insignificant improvements in yield have a significant effect on the operational costs for producing molecular sieve catalyst on a commercial scale due to the volume of catalyst that is needed to operate an OTO plant on this scale. In addition, with respect to the prime olefin selectivity (POS), this again is a significant parameter and, even though seemingly insignificant improvements in the POS may be obtained on a laboratory scale, when scaled up to a commercial scale, again these differences are very significant.

For a silico-alumina molar ratio varying between 0.05 or 0.10 to 0.15 or 0.20 or 0.30 or 0.35 in combination with the aforesaid structure directing agent to alumina molar ratio and in combination with the water to alumina molar ratio, the yield and prime olefins selectivity are particularly improved in comparison to molecular sieves which are synthesized from mixtures in which any one of these respective ratios are outside these ranges.

The silica sources may comprise a colloidal silica, a fumed silica, an amorphous silica, or an organic silica, such as a tetraalkyl orthosilicate. Suitable organic silica sources are tetraethylorthosilicate (TEOS), tetramethylorthosilicate (TMOS), or the like, or a combination thereof. A desirable amorphous silica is Baker silica as supplied by J T Baker. This is a synthetic amorphous silica. A desirable colloidal silica is Ludox™ as supplied by W R Grace & Co.

In a preferred embodiment, the source of silica is in the form of a colloidal silica. These silica sources provide an improved yield in comparison to the aforesaid non-colloidal silica sources.

In a further embodiment, the water to alumina molar ratio in the synthesis mixture may vary between 10 and 40, preferably between 12 and 38, more preferably between 14 and 35, even more preferably between 18 and 34. Most preferably, the water to alumina molar ratio in the synthesis mixture may vary between 20 and 30.

In an embodiment, the template to alumina molar ratio in the mixture may vary between 10 and 40, preferably between 12 and 38, more preferably between 14 and 35, even more preferably between 18 and 34. Most preferably, the water to alumina molar ratio in the synthesis mixture may vary between 20 and 30.

Any organic directing agent capable of directing the synthesis of CHA framework type molecular sieves can be employed, but generally the structure directing agent is a compound having the formula (I):

$$R^1R^2N-R^3 \quad (I)$$

wherein $R^1$ and $R^2$ are independently selected from the group consisting of alkyl groups having from 1 to 3 carbon atoms and hydroxyalkyl groups having from 1 to 3 carbon atoms and $R^3$ is selected from the group consisting of 4- to 8-membered cycloalkyl groups, optionally substituted by 1 to 3 alkyl groups having from 1 to 3 carbon atoms; and 4- to 8-membered heterocyclic groups having from 1 to 3 heteroatoms, said heterocyclic groups being optionally substituted by 1 to 3 alkyl groups having from 1 to 3 carbon atoms and the heteroatoms in said heterocyclic groups being selected from the group consisting of O, N, and S. Examples of suitable structure directing agents are N,N-dimethylcyclohexylamine (DMCHA), dipropylamine, morpholine, tetraethylammoniumhydroxide (TEAOH), and/or combinations of the aforesaid structure directing agents. A preferred structure directing agent is DMCHA.

The sources of alumina and phosphorus suitable for use in the present invention are typically those known in the art or as described in the literature for the production of aluminophosphates and silicoaluminophosphates. For example, the alumina source may be an aluminum oxide (alumina), optionally hydrated, an aluminum salt, especially a phosphate, an aluminate, or a mixture thereof. Other sources may include alumina sols or organic alumina sources, e.g., aluminum alkoxides such as aluminum isopropoxide. A preferred source is a hydrated alumina, most preferably pseudoboehmite, which contains 75% $Al_2O_3$ and 25% $H_2O$ by weight.

Typically, the source of phosphorus is a phosphoric acid, especially orthophosphoric acid, although other phosphorus sources, for example, organophosphates (e.g., trialkylphosphates such as triethylphosphate) and aluminophosphates may be used. When organophosphates and/or aluminophosphates are used, typically they are present collectively in a minor amount (i.e., less than 50% by weight of the phosphorus source) in combination with a majority (i.e., at least 50% by weight of the phosphorus source) of an inorganic phosphorus source (such as phosphoric acid).

The reaction mixture may also contain seeds to facilitate the crystallization process. The amount of seeds employed can vary widely, but generally the reaction mixture comprises from 0.01 ppm by weight to 10,000 ppm by weight, such as from 100 ppm by weight to 5,000 ppm by weight of said seeds. Generally, the seeds can be homostructural with the desired product that is solely of a CHA framework type material. Heterostructural seeds of, for example, an AEI, LEV, ERI, AFX, or OFF framework-type molecular sieve, or a combination or intergrowth thereof, may also be used. The seeds may be added to the reaction mixture as a suspension in a liquid medium, such as water; in some cases, particularly where the seeds are of relatively small size, the suspension can be colloidal. The production of colloidal seed suspensions and their use in the synthesis of molecular sieves are disclosed in, for example, International Publication Nos. WO 00/06493 and WO 00/06494, both of which are incorporated herein by reference.

Crystallization of the reaction mixture is carried out under either static or stirred conditions in a suitable reactor vessel.

In an embodiment, the synthesis mixture is heated at a heat up rate of between 20° C./hour to 120° C./hour, preferably ranging from 30° C./hour to 110° C./hour, and more preferably from 40° C./hour to 80° C./hour. The synthesis mixture is heated to a crystallization temperature of from 100° C. to 250° C., preferably from 150° C. to 200° C. In an embodiment of the invention, when the desired crystallization temperature is reached, this temperature is maintained for a period of time ranging from 20 minutes to 350 hours, more preferably from 60 minutes to 200 hours. Most preferably the crystallization temperature is maintained up to 150 hours, preferably up to 120 hours or up to 100 hours or up to 80 hours, or up to 24 hours or up to 16 hours or up to 12 hours or up to 8 hours or up to 4 hours or up to 2 hours. Following heating to a crystallization temperature the synthesis mixture is allowed to cool. Following cooling, the crystalline product can be recovered by standard means such as by centrifugation or filtration and the product may then be washed and dried. Crystallization may be conducted whilst stirring or, alternatively, crystallization may be conducted whilst the mixture is held stationary.

In another embodiment, the crystal size of the as-synthesized catalyst may vary between 0.5 to 2 µm, preferably between 0.7 to 1.8 µm and more preferably between 0.9 to 1.7 µm. The crystallized silicoaluminophosphate molecular sieve may have a crystal size distribution such that its average crystal size is no more than 5.0 µm, preferably no more than 3.0 µm, for example no more than 2.0 µm or no more than 1.5 µm.

As used herein, the term "average crystal size," with respect to a crystal size distribution, should be understood to refer to a measurement on a representative sample or an average of multiple samples that together form a representative sample. Average crystal size can be measured by SEM, in which case the crystal size of at least 30 crystals must be measured in order to obtain an average crystal size, and/or average crystal size can be measured by a laser light scattering particle size analyzer instrument, in which case the measured $d_{50}$ of the sample(s) can represent the average crystal size. It should also be understood that, while many of the crystals disclosed herein are relatively uniform (for instance, very close to cubic, thus having little difference between diameter measured along length, height, or width, e.g., when viewed in a SEM), the "average crystal size," when measured visually by SEM, represents the longest distance along one of the three-dimensional orthogonal axes (e.g., longest of length, width/diameter, and height, but not diagonal, in a cube, rectangle, parallelogram, ellipse, cylinder, frusto-cone, platelet, spheroid, or rhombus, or the like).

However, the $d_{50}$, when measured by light scattering in a particle size analyzer, is reported as a spherical equivalent diameter, regardless of the shape and/or relative uniformity of shape of the crystals in each sample. In certain circumstances, the $d_{50}$ values measured by the particle size analyzer may not correspond, even roughly, to the average crystal size measured visually by a representative SEM micrograph. Often in these cases, the discrepancy relates to an agglomeration of relatively small crystals that the particle size analyzer interprets as a single particle. In such circumstances, where the $d_{50}$ values from the particle size analyzer and the average crystal size from a representative SEM are significantly different, the representative SEM micrograph should be the more accurate measure of "average crystal size" and the average crystal size measurement is derived from the SEM micrograph.

Preferably, the $SiO_2/Al_2O_3$ ratio added to the synthesis mixture can be as close as possible to the $SiO_2/Al_2O_3$ ratio of the as-synthesized crystallized silicoaluminophosphate molecular sieve (e.g., difference between the $SiO_2/Al_2O_3$ ratio in the synthesis mixture and in the crystallized silicoaluminophosphate molecular sieve can be no more than 0.10, preferably no more than 0.08, for example no more than 0.07) and/or the synthesis mixture and the crystallized silicoaluminophosphate molecular sieve can both exhibit a relatively low $SiO_2/Al_2O_3$ ratio (e.g., both can be less than 0.33, preferably less than 0.30, for example no more than 0.25, no more than 0.20, no more than 0.15, or no more than 0.10).

In a preferred embodiment, the order of addition of the components in the mixture (i.e., in step (a)) is advantageously tailored, e.g., to provide better homogeneity. For instance, step (a) may comprise: (i) combining the source of phosphorus and the source of alumina, optionally with a liquid mixture medium, to form a primary mixture; (ii) aging the primary mixture for an aging time and under aging conditions (e.g., at an aging temperature), preferably sufficient to allow homogenization of the primary mixture, physico-chemical interaction between the source of phosphorus and the source of alumina, or both; and (iii) adding the source of silicon, the at least one organic template, and optionally additional liquid mixture medium, to the aged primary mixture to form the synthesis mixture. In certain cases of this embodiment, within step (iii), said source of silica is combined with said primary mixture prior to adding said at least one organic template or structure directing agent. Advantageously, said primary mixture and said source of silica can be combined to form a secondary mixture for a time and under conditions (e.g., temperature) sufficient to allow homogenization of the secondary mixture, physico-chemical interaction between said source of silica and said primary mixture, or both, after which said at least one organic template is combined therewith.

In a further embodiment, there is provided a silicoaluminophosphate molecular sieve which is prepared in accordance with any one of the methods as hereinbefore described. The sieve may be crystallized from a synthesis mixture comprising a colloidal source of silica ($SiO_2$), a source of phosphorus, a source of alumina ($Al_2O_3$), water ($H_2O$), a DMCHA structure directing agent (R) and optionally seeds, wherein the molar ratio of structure directing agent relative to the source of alumina R/Al$_2$O$_3$ ranges from 1.3 to 1.9 and the molar ratio of water to the source of alumina H$_2$O/Al$_2$O$_3$ ranges from 18 to 34, said sieve comprising a crystal size distribution such that the average crystal size is between 0.7 to 2.2 µm, preferably between 0.9 to 2.0 µm. The silica to alumina molar ratio Si/Al$_2$O$_3$ in the mixture ranges from 0.10 to 0.15.

The molecular sieve may be used to convert hydrocarbons into olefins by formulating the silicoaluminophosphate molecular sieve along with a binder and optionally a matrix material into a silicoaluminophosphate molecular sieve catalyst composition comprising from at least 10% to 50% of molecular sieve, and contacting said catalyst composition with a hydrocarbon feed under conditions sufficient to convert said hydrocarbon feed into a product comprising predominantly one or more olefins.

Materials which may be blended with the present molecular sieve material include a large variety of inert, catalytically inactive materials. These materials include compositions such as kaolin and/or other clays, one or more earth metals other than zeolite catalyst components, zeolite catalyst components alumina, titania, zirconia, cobalt, silica or silica sol, and mixtures thereof. These components are also effective to reduce overall catalyst cost, improve heat resistance during regeneration, and to increase catalyst strength. When blended with such components, the amount of CHA-containing crystalline material in the final catalyst product ranges from 10 to 90 wt % of the total catalyst, preferably 20 to 80 wt % of the total catalyst. The catalyst is particularly suited to convert hydrocarbons in the form of oxygenates to one or more olefins, particularly ethylene and propylene.

As used herein the term "oxygenates" is defined to include, but it is not necessarily limited to, alcohol, ethers, carbonyl compounds (aldehydes, ketones, carboxylic acid, carbonate endelites), and also compounds containing hetero-atoms, such as halides, mercaptans, sulfides, amines, and mixtures thereof. The oxygenates may contain from 1 to 10 carbon atoms, preferably from 1 to 4 carbon atoms. The representative oxygenates include lower straight chained branched alcohols, and their unsaturated counterparts.

Examples of suitable oxygenate compounds may include, but are not necessarily limited to: methanol; ethanol; n-propanol; isopropanol; C$_4$ to C$_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines; n-alkyl halides; n-alkyl sulfides having n-alkyl groups comprising from 3-10 carbon atoms; and the like; and mixtures thereof. Particularly suitable oxygenate compounds are methanol, dimethyl ether, and mixtures thereof, and most preferably comprise methanol. As used herein, the term "oxygenate" designates only the organic material used as the feed. The total charge of feed to the reaction zone may contain additional compounds, such as diluents.

A wide range of weight hourly space velocities (WHSV) for the feedstock may be selected in the oxygenate conversion process. WHSV is defined as weight of feed (excluding diluents) per hour per weight of a total reaction volume of molecular sieve catalyst (excluding inert components and/or fillers). In certain embodiments, the WHSV is generally in the range from 0.01 hr$^{-1}$ to 500 hr$^{-1}$, such from 0.5 hr$^{-1}$ to 300 hr$^{-1}$, for example from 0.1 hr$^{-1}$ to 200 hr$^{-1}$.

The invention will now be described by way of example only and with reference to the following Examples and accompanying drawings.

The analysis techniques described below were among those used in characterizing various samples from the Examples.

ICP-OES

Elemental component analysis has been done using ICP-OES (Inductively Coupled Plasma-Optical Emission Spectrometry). Samples were dissolved in a mixture of acids and diluted in de-ionised water and were analyzed using a VISTA-MPX instrument from Varian. This instrument was calibrated using commercially available standards (typically at least 3 standards and a blank). The power used was about 1.2 kW, plasma flow about 13.5 L/min, and nebulizer pressure about 200 kPa for all lines. Results are expressed in wt % or ppm by weight (wppm), and the values are recalculated to Si/Al$_2$ molar ratios.

XRD

Two X-ray diffractometers were used: a STOE Stadi-P Combi Transmission XRD and a Scintag X2 Reflection XRD with optional sample rotation. Cu—K$_\alpha$ radiation was used. Typically, a step size of 0.2°2Θ and a measurement time of about 1 hour were used.

SEM

A JEOL JSM-6340F Field-Emission-Gun scanning electron microscope (SEM) was used, operating at about 2 kV and about 12 µA. Prior to measurement, samples were dispersed in ethanol, subjected to ultrasonic treatment for about 5 to about 30 minutes, deposited on SEM sample holders, and dried at room temperature and pressure (about 20-25° C. and about 101 kPa). If an average particle size was determined based on the SEM micrographs, typically the measurement was performed on at least 30 crystals. In case of near cubic crystals, the average was based on the sizes of one of the edges of each crystal.

PSA

Particle size analysis was performed using a Mastersizer APA2000 from Malvern Instruments Limited, equipped with a 4 mW laser beam, based on laser scattering by randomly moving particles in a liquid medium. The samples to be measured were dispersed in water under continuous ultrasonic treatment to ensure proper dispersion. The pump speed applied was 2000 RPM, and the stirrer speed was 800 RPM. The parameters used in the operation procedure were: Refractive Index=1.544, Absorption=0.1. The results were calculated using the "general purpose-enhanced sensitivity" model. The results were expressed as d$_{50}$, meaning that 50 vol % of the particles were smaller than the value. The d$_{50}$ measurements were taken as an average of at least 2 measurements, with a delay of at least about 10 seconds between the measurements.

COMPARATIVE EXAMPLE A

This Example illustrates the synthesis of a molecular sieve using an organic silica source and selecting a water to alumina molar ratio H$_2$O/Al$_2$O$_3$ which is outside the preferred range.

Synthesis mixtures A-1, A-2, A-3 and A-4 were prepared using TEOS as organic silica source. The alumina source was Condea Pural™ alumina The source of phosphorous was a solution of H$_3$PO$_4$ at a concentration of 56 wt %. The template R was dimethylcyclohexylamine (DMCHA). Synthesis samples were prepared in the following ratios:

0.15 SiO$_2$/0.75P$_2$O$_5$/Al$_2$O$_3$/xR/yH$_2$O

For the runs in this example, the template R to alumina molar ratio x was varied between 1.5 and 1.35. Furthermore, the molar ratio y of water to alumina was varied between 35 and 40.

The synthesis mixtures were prepared in Teflon containers. First the silica was added. Subsequently, distilled water and diluted phosphoric acid were added to the containers whilst stirring and the alumina and template were also added whilst stirring. SAPO-34 seeds were added at varying concentrations of 100 and 400 ppm as set out in the below Table 1. The mixtures were heated at a heat-up rate of 20° C./hour to a crystallization temperature of 175° C. The mixtures were held at this temperature for 120 hours.

Synthesis mixtures A1, A2, A3 and A4 were prepared by mixing the relevant components as listed above with varying ratios for the seed content, water content and template content as set out in the below Table 1. The synthesized sieves in all of the sample mixtures contained 100% of chabazite (CHA) crystals. Table 1 lists the yield of the compositions.

TABLE 1

Comparative Example A

| Sample | DMCHA/Al$_2$O$_3$ | H$_2$O/Al$_2$ | Seeds (ppm) | Phase (XRD) | Yield (wt %) |
|---|---|---|---|---|---|
| A1 | 1.5 | 35 | 100 | CHA | 11 |
| A2 | 1.5 | 40 | 400 | CHA | 11 |
| A3 | 1.35 | 35 | 100 | CHA | 13.5 |
| A4 | 1.35 | 40 | 400 | CHA | 12 |

EXAMPLE B

In this example, synthesis mixtures using various silica sources were prepared. Baker silica was used as a precipitated silica source, TEOS was used as an organic silica source and Ludox was used as a colloidal silica source. The alumina source was Condea Pural alumina The source of phosphorous was a solution of H$_3$PO$_4$ at a concentration of 56 wt %. The template R was dimethylcyclohexylamine (DMCHA). Synthesis samples were prepared in the following ratios:

xSiO$_2$/P$_2$O$_5$/Al$_2$O$_3$/1.7R/30H$_2$O

In the samples of this Example, the silica to alumina molar ratios x were varied between 0.1 to 0.15 together with the sources of silica. The water content of the mixtures was maintained at a molar ratio of 30H$_2$O/Al$_2$O$_3$. All synthesis mixtures were prepared in Teflon containers at 10° C. Distilled water and diluted phosphoric acid were added to the containers whilst stirring. These solutions were mixed for five minutes before the alumina powder was added. When the alumina was added, the mixtures were stirred for 1 hour. The relevant silica sources, either TEOS, or Baker's silica or Ludox AS40 were added whilst stirring was continued. The mixtures were stirred for another hour before the template was added. The mixtures were again stirred for a further 10 minutes, and then SAPO-34 seeds were added at a concentration of 400 ppm. The final synthesis mixture was homogenized for another 10 minutes before inserting the containers into an autoclave.

The mixtures were aged for a further hour whilst stirring at 22° C. in closed reactors. Subsequently, the mixtures were heated to the crystallization temperature of 160° C. at a heat up rate of 100° C. per hour. The mixtures were maintained at the crystallization temperature whilst stirring for a duration of 144 hours. After this time, the reactors were cooled to room temperature and the solid was separated from the liquid by centrifuging and subsequent wash cycles with de-ionized water. The yields of the syntheses were expressed as recovered dry molecular sieve recovered (in wt %) based on the total weight of the initial synthesis mixture.

Figure 2:
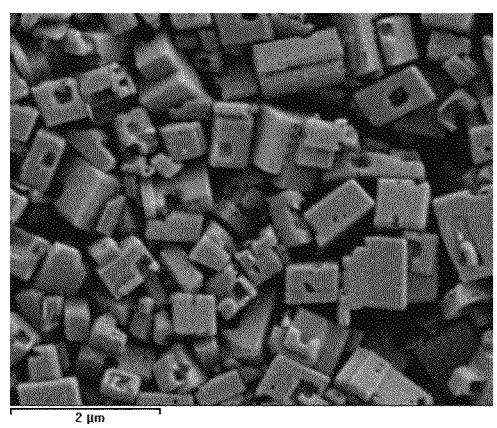
FIG. 2 shows a SEM corresponding to a molecular sieve sample as prepared in accordance with Example B for Sample B8.
Figure 3:
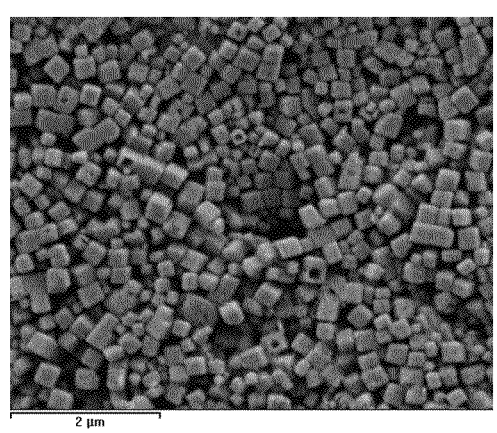
FIG. 3 shows a SEM corresponding to a molecular sieve sample as prepared in accordance with Example B for Sample B11.

All the XRD patterns for the samples were indicative of a pure CHA sieve material. FIGS. 1, 2 and 3 show SEM pictures for the sieves of Sample B4 (made with Baker's silica), Sample B8 (made with Ludox) and Sample B11 (made with TEOS). From the pictures, it is immediately evident that the physical shape of the synthesized crystals differs depending on the type of silica source. Table 2 summarizes the results of the experiments. The d$_{50}$ measurement in Table 2 was verified by reference to the SEM pictures for the samples.

TABLE 2

Example B.

| Sample | Si/Al$_2$O$_3$ x (mix) | Silica source | d$_{50}$ micron | Yield wt % | Si/Al$_2$O$_3$ (product) | Average POS (wt %) |
|---|---|---|---|---|---|---|
| B1 | 0.10 | Baker | 1.1 | 11.0 | 0.16 | 78.5 |
| B2 | 0.11 | Baker | 0.5 | 12.3 | 0.15 | 78.6 |
| B3 | 0.12 | Baker | 0.5 | 13.0 | 0.16 | 78.8 |
| B4 | 0.15 | Baker | 0.5 | 15.3 | 0.18 | 78.3 |
| B5 | 0.10 | Ludox | 1.1 | 15.2 | 0.14 | 79.2 |
| B6 | 0.11 | Ludox | 1.2 | 16.3 | 0.15 | 79.3 |
| B7 | 0.12 | Ludox | 1.7 | 18.5 | 0.14 | 79.4 |
| B8 | 0.15 | Ludox | 1.2 | — | 0.17 | 79.4 |
| B9 | 0.10 | TEOS | 0.5 | 13.0 | 0.14 | 78.8 |
| B10 | 0.11 | TEOS | 0.4 | 13.9 | 0.16 | 78.8 |
| B11 | 0.12 | TEOS | 0.4 | 16.5 | — | 78.4 |
| B12 | 0.15 | TEOS | 0.4 | 15.4 | 0.18 | 77.9 |

Table 2 lists the d$_{50}$ values as generated by Malvern laser sizing equipment. This Table confirms that material made with TEOS as silica source has the smallest crystals. The materials made with Ludox as silica source have the largest crystals and the highest yield.

To test the as-synthesized catalyst samples, they were calcined in order to remove the template. The oven temperature was ramped from room temperature to 150° C. at a heat up rate of 2° C. per minute in a nitrogen environment. Before switching to air flow, the oven was held at 150° C. for 0.5 hours. Subsequently, the oven temperature was ramped up at 3° C. per minute to a temperature of 650° C. and the catalysts were calcined in air at 650° C. for 2 hours. The calcined samples were loaded into the reactors for testing.

The reactors were one quarter inch stainless steel tubes with silicon coated inner walls. The catalyst was mixed with SiC before being packed into the tubular reactor for better heat transfer properties. The SiC particles were 200 to 450 μm in diameter. Typically the SiC loading was 200 milligrams. The packed reactors were put in to a heat chamber to be tested. All the materials were tested at one process condition, at a pressure of 172 kPag (25 psig), an operation temperature of 500° C. and a feedstock flow rate of 100 WHSV. The catalyst was exposed to methanol in a fresh to death run for 20 minutes.

The reaction products for each of the samples were analyzed by a fast gas chromatograph (GC) which detected hydrocarbons and oxygenates. The average selectivities for ethylene and propylene (POS) are also listed in Table 2.

EXAMPLE C

This Example explores the effect of the silica source, the silica to alumina ratio and the effect of the heat up rate during the synthesis of the sieve mixture.

Synthesis mixtures using various silica sources were prepared. Baker's silica was used as a precipitated silica source, TEOS was used as an organic silica source and Ludox was used as a colloidal silica source. The alumina source was Condea Pural alumina. The source of phosphorous was a solution of $H_3PO_4$ at a concentration of 56 wt %. The template R was DMCHA. Synthesis samples were prepared in the following ratios:

$xSiO_2/P_2O_5/Al_2O_3/1.7R/30H_2O$

For the samples in this Example, the silica to alumina molar ratios x were varied between 0.1 to 0.15 together with the sources of silica. The water content of the mixtures were maintained at a molar ratio of $30H_2O$ to $Al_2O_3$. All synthesis mixtures were prepared in Teflon containers at 10° C. Distilled water and diluted phosphoric acid were added to the containers whilst stirring. This solution was mixed for five minutes before the alumina powder was added. When the alumina was added, the mixture was stirred for 1 hour. The relevant silica sources, either TEOS, or Baker's silica or Ludox AS40 were added whilst stirring was continued. The mixtures were stirred for another hour before the template was added. These mixtures were again stirred for a further 10 minutes, and then SAPO-34 seeds were added at a concentration of 400 ppm. The final synthesis mixture was homogenized for another 10 minutes before inserting the containers into an autoclave.

Subsequently, the mixtures for samples L1-L12 were heated to the crystallization temperature of 160° C. at a heat up rate of 40° C. per hour. The mixtures were maintained at the crystallization temperature whilst stirring for a duration of 144 hours. After this time, the reactors were cooled to room temperature and the solid was separated from the liquid by centrifuging and subsequent wash cycles with de-ionized water. The yield of the synthesis was expressed as recovered dry molecular sieve recovered (in wt %) based on the total weight of the initial synthesis mixture.

Tables 3 summarizes the results of these experiments. All the XRD patterns for the samples were indicative of a pure CHA sieve material.

TABLE 3

Heat up rate to crystallization temperature 40° C./hour.

| Sample no. | $Si/Al_2O_3$ X (mixture) | Silica | $d_{50}$ micron | yield % | $Si/Al_2O_3$ (sieve) | Average POS (wt %) |
|---|---|---|---|---|---|---|
| L1 | 0.10 | Baker | 0.40 | 10.9 | 0.17 | 77.8 |
| L2 | 0.11 | Baker | 0.40 | 11.9 | 0.17 | 77.9 |
| L3 | 0.12 | Baker | 0.50 | 13.1 | 0.17 | 75.9 |
| L4 | 0.15 | Baker | 0.50 | 16.4 | 0.19 | 76.9 |
| L5 | 0.10 | Ludox | 1.50 | 16.8 | 0.13 | 79.5 |
| L6 | 0.11 | Ludox | 1.10 | 16.7 | 0.14 | 79.8 |
| L7 | 0.12 | Ludox | 1.00 | 16.3 | 0.15 | 79.4 |
| L8 | 0.15 | Ludox | 0.90 | 17.2 | 0.17 | 79.2 |
| L9 | 0.10 | TEOS | 0.30 | 11.1 | 0.18 | 78.0 |
| L10 | 0.11 | TEOS | 0.40 | 13.5 | 0.18 | 77.2 |
| L11 | 0.12 | TEOS | 0.40 | 12.9 | 0.19 | 77.6 |
| L12 | 0.15 | TEOS | 0.40 | 14.0 | 0.19 | 78.1 |

To test the as-synthesized catalyst samples L1-L12, the samples were calcined to remove the template. The oven temperature was ramped from room temperature to 150° C. at a heat up rate of 2° C. per minute in a nitrogen environment. Before switching to air flow, the oven was held at 150° C. for 0.5 hours. Subsequently, the oven temperature was ramped up at 3° C. per minute to a temperature of 650° C. and the catalysts were calcined in air at 650° C. for 2 hours. The calcined samples were loaded into the reactors for testing.

The reactors were one quarter inch stainless steel tubes with silicon coated inner walls. The catalyst was mixed with SiC before being packed into the tubular reactor for better heat transfer properties. The SiC particles were 200 to 450 μm in diameter. Typically the SiC loading was 200 milligrams. The packed reactors were put in to a heat chamber to be tested. All the materials were tested at one process condition, at a pressure of 172 kPag (25 psig), an operation temperature of 500° C. and a feedstock flow rate of 100 WHSV. The catalyst was exposed to methanol in a fresh to death run for 20 minutes.

The reaction products for each of the samples were analyzed by a fast gas chromatograph (GC) which detected hydrocarbons and oxygenates and prime olefin selectivity (POS) in wt % of the reaction products was determined.

Table 3 shows that the highest molecular sieve yields are achieved with Ludox as a colloidal silica source. Furthermore, the Ludox based sieves have a higher POS than the sieves which are synthesized from Baker's silica or TEOS as silica sources. Also, Table 3 shows that molecular sieves which are synthesized from a Ludox silica source, have a larger crystal size than molecular sieves which are synthesized from mixtures containing a precipitated silica (Baker's silica) or an organic silica (TEOS) as silica source.

EXAMPLE D

In this example, synthesis mixtures were prepared using TEOS as an organic silica source. The alumina source was Condea Pural alumina The source of phosphorous was a solution of $H_3PO_4$ at a concentration of 56 wt %. The template R was DMCHA. Synthesis sample mixtures were prepared in the following ratios:

$0.15SiO_2/P_2O_5/Al_2O_3/xR/yH_2O$ and 400 ppm of SAPO-34 seeds

The ratio of template R to alumina $Al_z$ was varied between 1.7, 1.8 and 2 and the $H_2O/Al_2O_3$ ratio y was varied between 16 and 30 for the various mixture samples. All synthesis mixtures were prepared in Teflon™ containers. Distilled water and diluted phosphoric acid were added to the containers whilst stirring. This solution was mixed for five minutes before the alumina powder was added. When the alumina was added, the mixtures were stirred for 1 hour. The TEOS silica was added whilst stirring was continued. The mixtures were stirred for another hour before the template was added. The mixtures were again stirred for a further 10 minutes, and then SAPO-34 seeds were added at a concentration of 400 ppm. The final synthesis mixtures were homogenized for another 10 minutes before inserting the containers into an autoclave.

Subsequently, the mixtures for the samples were heated to the crystallization temperature of 160° C. at a heat up rate of 40° C. per hour. The mixtures were maintained at the crystallization temperature whilst stirring for a duration of 144 hours. After this time, the reactors were cooled to room temperature and the solid was separated from the liquid by centrifuging and by subsequent wash cycles with de-ionized water. The yields of the syntheses were expressed as recovered dry molecular sieve (in wt %) based on the total weight of the initial synthesis mixture.

Table 4 presents the yields of the synthesized sieves as a function of the water to alumina ratio (a) and the template to water ratio (b).

TABLE 4

Example D.

| Sample no. | R/Al$_2$O$_3$ | H$_2$O/Al$_2$O$_3$ | Si/Al$_2$O$_3$ (sieve) | Yield (wt %) | Average POS (wt %) |
|---|---|---|---|---|---|
| 1 | 2.0 | 30 | 0.27 | 11.6 | 78.8 |
| 2 | 2.0 | 20 | 0.30 | 12.8 | 78.3 |
| 3 | 2.0 | 18 | 0.30 | 12.7 | 78.3 |
| 4 | 2.0 | 16 | 0.27 | 12.8 | 78.5 |
| 5 | 1.8 | 30 | 0.24 | 14.7 | 78.8 |
| 6 | 1.8 | 20 | 0.28 | 15.9 | 78.1 |
| 7 | 1.8 | 18 | 0.28 | 15.2 | 78.1 |
| 8 | 1.8 | 16 | 0.27 | 11.5 | 78.9 |
| 9 | 1.7 | 30 | 0.22 | 16.7 | 78.9 |
| 10 | 1.7 | 20 | 0.26 | 14.0 | 78.7 |
| 11 | 1.7 | 18 | 0.27 | 18.0 | 78.6 |
| 12 | 1.7 | 16 | 0.26 | 15.0 | 78.4 |

To test the as-synthesized catalyst samples of Example D, the samples were calcined and pretreated in the same way as the Samples in Example C. The reactors were one quarter inch stainless steel tubes with silicon coated inner walls. The catalyst was mixed with SiC before being packed into the tubular reactor for better heat transfer properties. The SiC particles were 200 to 450 μm in diameter. The SiC loading was 200 milligrams. The packed reactors were put in to a heat chamber to be tested. All the materials were tested at one process condition, at a pressure of 172 kPag (25 psig), a operation temperature of 500° C. and a feedstock flow rate of 100 WHSV. The catalyst was exposed to methanol in a fresh to death run for 20 minutes.

The reaction products for each of the samples were analyzed by a fast gas chromatograph (GC) which detected hydrocarbons and oxygenates and prime olefin selectivity (POS) in wt % of the reaction products was determined.

Table 4 lists the average POS at 500° C. for the catalyst samples obtained from the different synthesis mixtures.

COMPARATIVE EXAMPLE E

Similar to the preparation of the synthesis mixtures of Example D, synthesis mixtures were prepared having a silica to alumina ratio of 0.11 in the mixtures. All other synthesis conditions were held the same in this Example as in Example D. Table 5 presents the yields of the synthesized sieves as a function of the water to alumina ratio.

TABLE 5

Comparative Example E

| Sample no. | R/Al$_2$O$_3$ | H$_2$O/Al$_2$O$_3$ | Yield (wt %) |
|---|---|---|---|
| 1 | 2.0 | 30 | 8.5 |
| 2 | 2.0 | 20 | 8.3 |
| 3 | 2.0 | 18 | 9.1 |
| 4 | 2.0 | 16 | 9.4 |
| 5 | 1.8 | 30 | 9.4 |
| 6 | 1.8 | 20 | 10.1 |
| 7 | 1.8 | 18 | 9.1 |
| 8 | 1.8 | 16 | 7.8 |
| 9 | 1.7 | 30 | 14.0 |
| 10 | 1.7 | 20 | 10.4 |
| 11 | 1.7 | 18 | 9.6 |
| 12 | 1.7 | 16 | 4.9 |

There is thus provided a method of preparing a method of preparing a silicoaluminophosphate molecular sieve, from a source of silica, a source of phosphorus, a source of alumina, water, a structure directing agent and optional seeds whereby the molar ratio of structure directing agent relative to the source of alumina, and the ratio of water to the source of alumina are defined so as to optimize the yield of synthesized sieve whilst minimizing the use of template.

All documents as described herein are herein incorporated by reference, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby.

Now, having described the various features of the process for preparing the molecular sieves, and methods of using such in an oxygenate-to-olefins reaction, described herein in numbered embodiments is:

1. A method of preparing a silicoaluminophosphate molecular sieve, comprising:
   (a) combining a source of silica (SiO$_2$), a source of phosphorus, a source of alumina (Al$_2$O$_3$), and water (H$_2$O) to form a primary mixture;
   (b) adding a structure directing agent (R) to said mixture and optional seeds to form a synthesis mixture; followed by
   (c) heating said synthesis mixture to a crystallization temperature to form the molecular sieve; and
   wherein the molar ratio of structure directing agent relative to the source of alumina R/Al$_2$O$_3$ ranges from 1.3 to 1.9 and the molar ratio of water to the source of alumina H$_2$O/Al$_2$O$_3$ ranges from 18 to 34.

2. The method of embodiment 1, wherein the silica to alumina ratio SiO$_2$/Al$_2$O$_3$ ranges from 0.10 to 0.15.

3. The method of embodiment 1 or 2, wherein the source of silica is in the form of a colloidal silica source.

4. The method of any of the preceding numbered embodiments, wherein the structure directing agent comprises N,N-dimethylcyclohexylamine (DMCHA), dipropylamine, morpholine, tetraethylammoniumhydroxide (TEAOH), and/or combinations of the aforesaid structure directing agents.

5. The method of any of the preceding numbered embodiments, wherein the crystallized molecular sieve has a crystal size distribution such that the average crystal size as measured from SEM micrographs, is between 0.7 to 2.2 μm, preferably between 0.9 to 2.0 μm.

6. The method of any of the preceding numbered embodiments, wherein the molar ratio of water to the source of alumina H$_2$O/Al$_2$O$_3$ ranges from 20 to 30.

7. The method of any of the preceding numbered embodiments, wherein the synthesis mixture is heated to the crystallization temperature at a heat up rate of ranging from 20° C./hr to 120° C./hr, preferably from 30° C./hr to 60° C./hr.

8. The method of any of the previous numbered embodiments, wherein said crystallization temperature ranges from 150° C. to 200° C.

9. The method of any of the previous numbered embodiments, wherein, within step (a), said primary mixture is formed in two stages, in a first stage a mixture is formed by combining a source of phosphorus, a source of alumina (Al$_2$O$_3$), and water (H$_2$O), in a second stage, the silica is combined with said first stage mixture to form said primary mixture prior to adding the structure directing agent in step b).

10. The method of any of the preceding numbered embodiments, wherein the seeds are present at a concentration of between 50 to 500 ppm, preferably between 350 to 450 ppm, based on the total weight of the synthesis mixture.

11. A silicoaluminophosphate molecular sieve crystallized from a synthesis mixture comprising a source of silica ($SiO_2$), a source of phosphorus, a source of alumina ($Al_2O_3$), water ($H_2O$), a structure directing agent (R) and optionally seeds, wherein the molar ratio of structure directing agent relative to the source of alumina $R/Al_2O_3$ ranges from 1.3 to 1.9 and the molar ratio of water to the source of alumina $H_2O/Al_2O_3$ ranges from 18 to 34, said molecular sieve comprising a crystal size distribution such that the average crystal size as determined from SEM micrographs, is between 0.7 to 2.2 µm, preferably between 0.9 to 2.0 µm.

12. A sieve according to embodiment 11, wherein the silica source comprises a colloidal silica source.

13. A method of converting hydrocarbons into olefins comprising:
    (a) preparing a silicoaluminophosphate molecular sieve according to the method of any of the previous claims 1 to 10;
    (b) formulating said silicoaluminophosphate molecular sieve, along with a binder and optionally a matrix material, into a silicoaluminophosphate molecular sieve catalyst composition comprising from at least 10% to 50% molecular sieve; and
    (c) contacting said catalyst composition with a hydrocarbon feed under conditions sufficient to convert said hydrocarbon feed into a product comprising predominantly one or more olefins.

14. A method of forming an olefin-based polymer product comprising:
    (a) preparing a silicoaluminophosphate molecular sieve according to the method of any of numbered embodiments 1-10;
    (b) formulating said silicoaluminophosphate molecular sieve, along with a binder and optionally a matrix material, into a silicoaluminophosphate molecular sieve catalyst composition comprising from at least 10 wt % to 50 wt % molecular sieve based on the total weight of the sieve composition;
    (c) contacting said catalyst composition with a hydrocarbon feed under conditions sufficient to convert said hydrocarbon feed into a product comprising predominantly one or more olefins; and
    (d) polymerizing at least one of the one or more olefins, optionally with one or more other comonomers and optionally in the presence of a polymerization catalyst, under conditions sufficient to form an olefin-based (co) polymer.

15. The method of embodiments 13 or 14, wherein the hydrocarbon feed is an oxygenate-containing feed comprising methanol, dimethylether, or a combination thereof, wherein the one or more olefins comprises ethylene, propylene, or a combination thereof, and wherein, as applicable, the olefin-based (co)polymer is an ethylene-containing (co)polymer, a propylene-containing (co)polymer, or a copolymer, mixture, or blend thereof 16. The method of any of the previous numbered embodiments, wherein the yield of the reaction to produce the silicoaluminophosphate molecular sieve is greater than 11 or 12 or 13%.

What is claimed is:

1. A silicoaluminophosphate molecular sieve crystallized from a synthesis mixture comprising a source of colloidal silica ($SiO_2$), a source of phosphorus, a source of alumina ($Al_2O_3$), water ($H_2O$), a structure directing agent (R) and optional seeds, wherein the molar ratio of structure directing agent relative to the source of alumina $R/Al_2O_3$ ranges from 1.3 to 1.9 and the ratio of water to the source of alumina $H_2O/Al_2O_3$ ranges from 20 to 34, said sieve comprising a crystal size distribution such that the average crystal size as measured from SEM micrographs, is between 0.7 to 2.2µm.

2. The sieve of claim 1, wherein the silica alumina ratio $SiO_2/Al_2O_3$ ranges from 0.10 to 0.15.

3. The sieve of claim 1, wherein the structure directing agent comprises N,N-dimethylcyclohexylamine (DMCHA), dipropylamine, morpholine, tetraethylammoniumhydroxide (TEAOH), and/or combinations of the aforesaid structure directing agents.

4. A method of preparing a silicoaluminophosphate molecular sieve, comprising:
    (a) combining a source of silica ($SiO_2$), a source of phosphorus, a source of alumina ($Al_2O_3$), and water ($H_2O$) to form a primary mixture, wherein the source of silica is in the form of a colloidal silica source;
    (b) adding a structure directing agent (R) to said mixture and optionally seeds to form a synthesis mixture; followed by (c) heating said synthesis mixture to a crystallization temperature to form the molecular sieve; and wherein the molar ratio of structure directing agent relative to the source of alumina $R/Al_2O_3$ ranges from 1.3 to 1.9 and the molar ratio of water to the source of alumina $H_2O/Al_2O_3$ ranges from 20 to 34.

5. The method of claim 4, wherein the structure directing agent comprises N,N-dimethylcyclohexylamine (DMCHA), dipropylamine, morpholine, tetraethylammoniumhydroxide (TEAOH), and/or combinations of the aforesaid structure directing agents.

6. The method of claim 4, wherein the crystallized silicoaluminophosphate molecular sieve has a crystal size distribution such that the average crystal size, as measured from SEM micrographs, ranges from 0.7 to 2.2µm.

7. The method of claim 4, wherein the synthesis mixture is heated to the crystallization temperature at a heat up rate ranging from 20° C./hr to 120° C./hr.

8. The method of claim 7, wherein the synthesis mixture is heated to the crystallization temperature at a heat up rate ranging from 30° C./hr to 60° C./hr.

9. The method of claim 4, wherein said crystallization temperature is between 150° C. and 200° C.

10. The method of claim 4, wherein, within step (a), said primary mixture is formed in two stages, in a first stage a mixture is formed by combining a source of phosphorus, a source of alumina ($Al_2O_3$), and water ($H_2O$), in a second stage, the silica is combined with said first stage mixture to form said primary mixture prior to adding the structure directing agent in step b).

11. The method of claim 4, wherein the seeds are present at a concentration of between 50 to 500 ppm based on the total weight of the synthesis mixture.

12. The method of claim 11, wherein the seeds are present at a concentration of between 350 to 450 ppm based on the total weight of the synthesis mixture.

13. A method of converting hydrocarbons into olefins comprising:
    (a) preparing a silicoaluminophosphate molecular sieve according to the method of claim 4;
    (b) formulating said silicoaluminophosphate molecular sieve, along with a binder and optionally a matrix material, into a silicoaluminophosphate molecular sieve catalyst composition comprising from at least 10% to 50% molecular sieve; and (c) contacting said catalyst composition with a hydrocarbon feed under conditions sufficient to convert said hydrocarbon feed into a polymer or (co)polymer product comprising predominantly one or more olefins.

14. The method of claim 13, wherein the hydrocarbon feed is an oxygenate-containing feed comprising methanol, dimethylether, or a combination thereof, wherein the one or more olefins comprises ethylene, propylene, or a combination thereof, and wherein, as applicable, the olefin-based (co)polymer is an ethylene-containing (co)polymer, a propylene-containing (co)polymer, or a copolymer, mixture, or blend thereof.

15. A method of forming an olefin-based polymer product comprising:
   (a) preparing a silicoaluminophosphate molecular sieve according to the method of claim 4;
   (b) formulating said silicoaluminophosphate molecular sieve, along with a binder and optionally a matrix material, into a silicoaluminophosphate molecular sieve catalyst composition comprising from at least 10% to 50% molecular sieve;
   (c) contacting said catalyst composition with a hydrocarbon feed under conditions sufficient to convert said hydrocarbon feed into a product comprising predominantly one or more olefins; and
   (d) polymerizing at least one of the one or more olefins, optionally with one or more other comonomers and optionally in the presence of a polymerization catalyst, under conditions sufficient to form an olefin-based (co)polymer.

16. The method of claim 15, wherein the hydrocarbon feed is an oxygenate-containing feed comprising methanol, dimethylether, or a combination thereof, wherein the one or more olefins comprises ethylene, propylene, or a combination thereof, and wherein, as applicable, the olefin-based (co)polymer is an ethylene-containing (co)polymer, a propylene-containing (co)polymer, or a copolymer, mixture, or blend thereof.

17. The method of claim 1, wherein the silica alumina ratio $SiO_2/Al_2O_3$ ranges from 0.10 to 0.15.

* * * * *